US010173057B2

(12) United States Patent
Dai (10) Patent No.: US 10,173,057 B2
(45) Date of Patent: Jan. 8, 2019

(54) DEVICE AND METHOD OF ELECTROPORATING DRUG-DELIVERING BY USING HOLLOW NEEDLE ELECTRODE

(71) Applicant: ETTA BIOTECH CO., LTD, Suzhou, Jiangsu (CN)

(72) Inventor: Edward Dai, Jiangsu (CN)

(73) Assignee: ETTA BIOTECH CO., LTD, Suzhou (CN)

( * ) Notice: Subject to any disclaimer, the term of this patent is extended or adjusted under 35 U.S.C. 154(b) by 142 days.

(21) Appl. No.: 15/126,360

(22) PCT Filed: May 11, 2015

(86) PCT No.: PCT/CN2015/078663
§ 371 (c)(1),
(2) Date: Sep. 15, 2016

(87) PCT Pub. No.: WO2015/139672
PCT Pub. Date: Sep. 24, 2015

(65) Prior Publication Data
US 2017/0080221 A1    Mar. 23, 2017

(30) Foreign Application Priority Data
Mar. 18, 2014    (CN) .......................... 2014 1 0099965

(51) Int. Cl.
*A61N 1/32* (2006.01)
*A61M 37/00* (2006.01)
(Continued)

(52) U.S. Cl.
CPC ............. *A61N 1/327* (2013.01); *A61M 5/142* (2013.01); *A61M 5/158* (2013.01); *A61M 37/00* (2013.01);
(Continued)

(58) Field of Classification Search
CPC ........ A61N 1/327; A61N 1/08; A61N 1/0476; A61N 1/0502; A61M 5/158; A61M 2037/0007
See application file for complete search history.

(56) References Cited

U.S. PATENT DOCUMENTS 5,273,525 A   12/1993   Hofmann
5,536,267 A    7/1996   Edwards et al.
(Continued)

FOREIGN PATENT DOCUMENTS

| CN | 1248923 | 3/2000 |
| CN | 1678369 | 10/2005 |

(Continued)

OTHER PUBLICATIONS

International search report dated Aug. 3, 2015 from corresponding application No. PCT/CN2015/078663.

*Primary Examiner* — Bradley J Osinski
(74) *Attorney, Agent, or Firm* — Hauptman Ham, LLP (57) ABSTRACT

An electroporating drug delivering device using hollow needle electrode includes a drug delivering head, a control console as well as a control line and a tube for connecting the drug delivering head and the control console. The drug delivering head includes a universal joint, a camera, an illuminating lamp, a molecular drug delivery structure, an electric connector, a grille, a hollow needle electrode array, and a stretchable structure. The control console includes a display for observing images, a rocker for controlling the universal joint, and a remote starting unit for controlling the generation of electric pulses. The control console is connected with the electric connector inside of the drug delivering head by the line arranged inside of the tube. The electroporating drug-administration device enhances the drug utilization efficiency and reduces the treatment time, and can accurately adjust the intensity and region of the electric field.

13 Claims, 3 Drawing Sheets

(51) Int. Cl.
*A61N 1/04* (2006.01)
*A61N 1/05* (2006.01)
*A61M 5/142* (2006.01)
*A61M 5/158* (2006.01)
*A61N 1/08* (2006.01)

(52) U.S. Cl.
CPC ......... *A61N 1/0476* (2013.01); *A61N 1/0502* (2013.01); *A61N 1/08* (2013.01); *A61M 2037/0007* (2013.01)

(56) References Cited

U.S. PATENT DOCUMENTS

| | | |
|---|---|---|
| 5,845,646 A | 12/1998 | Lemelson |
| 2011/0160514 A1 | 6/2011 | Long et al. |

FOREIGN PATENT DOCUMENTS

| | | |
|---|---|---|
| CN | 1768873 | 5/2006 |
| CN | 101495056 | 7/2009 |
| CN | 102091370 | 6/2011 |
| CN | 102905755 | 1/2013 |
| CN | 202920725 | 5/2013 |
| CN | 103861202 | 6/2014 |
| CN | 204147418 | 2/2015 |
| WO | 9422526 | 10/1994 |
| WO | 2013117306 | 8/2013 |

DEVICE AND METHOD OF ELECTROPORATING DRUG-DELIVERING BY USING HOLLOW NEEDLE ELECTRODE

RELATED APPLICATIONS

The present application is a National Phase of International Application Number PCT/CN2015/078663, filed May 11, 2015, and claims the priority of China Application No. 201410099965.0, filed Mar. 18, 2014, which are incorporated herein by reference in their entireties.

FIELD OF INVENTION

The present invention refers to a technology of introducing a molecular drug into tissues or cells by electroporation therapy (EPT), in particularly to, a method of delivering drugs or genes into tissues or cells by electroporation.

BACKGROUND OF THE INVENTION

It was found in 1970s that, electric fields can produce some pores on cells without causing permanent damages to the cells. This discovery made it possible for molecules to enter into the cytoplasm. People know that by means of the so-called electroporation, genes and other molecules such as drug compounds, are capable to be introduced into living cells. Genes or drugs as well as living cells are mixed in a buffer medium, and then applied with short pulses of a strong electric field. In this way, cell membranes transiently become porous, and then genes or molecules enter the cells. They can improve the genomes of the cells in there.

Drug compounds and genes are delivered into cells in vivo by electroporation therapy (EPT) utilizing the electric field, the electroporation therapy may also be referred as cell perforation therapy (CPT) or electrochemotherapy (ECT). Using cell perforation therapy for the treatment provides a way to avoid side effects usually accompanying with the use of anticancer drugs or cytotoxic agents. This treatment allows people to introduce these agents to selectively damage or kill the undesired cells, and meanwhile to avoid damaging or killing the surrounding healthy cells or tissues.

A therapeutic application of the electroporation is used in the treatment of cancers. Experiments have been carried out utilizing experimental mammals, and published reports are as follows: Okino, M., E. Kensuke, "*The Effects of a Single High Voltage Electrical Stimulation with an Anticancer Drug on in vivo Growing Malignant Tumors*", Jap. Journal of Surgery, vol. 20: 197-204, 1990. Mir, L. M., S. Orlowski, J. Belehradek Jr., and C. Paoletti, "*Electrochernotherapy Potentiation of Antitumor Effect of Bleomycin by Local Electric pulses*", Eur. J. Cancer, vol. 27: 68-72, 1991. Mir, L. M., M. Belehradek, C. Domengem, S. Orlowski, B. Poddevin, et al., have conducted clinical trials and published the report "*Electrochemotherapy, a novel antitumor treatment: first clinical trial*", C. R. Acad. Sci. Paris., vol 313: 613-618, 1991.

Electroporation in vivo is generally restricted to be applied on the tissues or cells near the skin of a living body, on which parts the electrode can be placed. Therefore, the electrode for electroporation generally cannot approach to tissues such as tumors which can be treated by the systemic drug delivery or chemotherapy. In the treatment of certain types of cancers by chemotherapy, it is needed to use a sufficient dose of drug to kill cancer cells on the premise of not killing too many normal cells. This purpose can be achieved if the chemotherapeutic drugs can be directly injected into the cancer cells. Some anticancer drugs, such as bleomycin, usually cannot effectively penetrate through cell membranes of some types of cancer cells. However, bleomycin can be injected into cells by electroporation.

The treatment method usually is, directly injecting an anticancer drug into the tumor, and then applying an electric field to the tumor between a pair of electrodes. The electric field intensity must be adjusted in appropriate accuracy so as to conduct electroporation on the tumor cells under the premise of not damaging the normal or healthy cells, or at least minimizing damages to the normal or healthy cells. For the tumor of the body surface, a pair of electrodes usually may be applied on two sides of the tumor to generate an electric field between the pair of electrodes, and thereby electroporation can be easily implemented. In the case of that the electric field is a uniform electric field, the distance between the electrodes is firstly measured, and then according to the formula E=V/d (E=electric field intensity in volts/centimeter; V=voltage in volts; d=distance in centimeter), an appropriate voltage is applied to the electrodes. When treating large tumors or tumors inside the body, it is difficult to properly place the electrodes and measure the distance between the electrodes. The above mentioned reports disclose an electrode system for electroporation in vivo, wherein the electrodes can be inserted into the tumor.

This therapeutic method is to directly penetrate an anticancer drug into the tumor, and to apply an electric field to the tumor located between the pair of electrodes. The electric field intensity must be adjusted reasonably and accurately, in order to achieve electroporation on tumor cells, without any damage to normal cells, i.e. healthy cells. This therapy usually is easy to implement for external tumors, and specific method is to place electrodes on two sides of the tumor so as to generate an electric field d between the electrodes. Then, the distance d between the electrodes is measured, and a suitable voltage is applied to the electrodes according to the formula E=V/d.

Researches have shown that large nucleotide sequences (up to 630 kb) can be introduced into mammalian cells by electroporation, and in this way, a gene therapeutic method is provided.

In a relevant U.S. Pat. No. 5,273,525, the injector for injecting molecules and macromolecules by electroporation is injection needle, and meanwhile, the injection needle plays the role of electrodes. This structure enables the electrode to work at the subcutaneous area. It is desired that an electrode device has an electrode capable of inserting into the tumor or getting close to the tumor, such that a predefined electric field required by electroporation on tumor cells can be generated in the tissue.

However, due to that the electric field generated by the electrode always is difficult to adjust during electroporation using the injector, and the nonuniform of the electric field intensity results in damages to a large amount of normal cells. Greater defects are, during actual operation, very difficult to operate an injector with an electrode, high requirement on operator, low drug utilization efficiency, and increased sufferings of the patients during treatment.

In order to overcome the above-mentioned disadvantages, the technical problems mainly solved by the present invention is to provide an electroporating drug-delivering device capable of entering human body with no damage or minimal damage, capable of monitoring in real time and accurately positioning, accurately controlling the administration dosage and depth, and capable of accurately adjust the electric field intensity. This device is a drug-delivering device for electroporation in vivo with a wide universality, a good electroporating effect and no chemical pollution, reducing damages to the normal cells, enhancing the drug utilization efficiency, reducing the treatment time and mitigating the sufferings of patients during treatment.

SUMMARY OF THE INVENTION

The present invention overcomes the above mentioned drawbacks of the prior art, and one of objectives of the present invention is to provide a drug-delivering device capable of monitoring the cell electroporation in real time, which comprises a drug delivering head and a control console. Another objective of the present invention is to provide a method for providing a uniform electric field and meanwhile delivering a molecular drug into cells.

To achieve the above mentioned purposes, the technical schemes of the device capable of monitoring the cell electroporation provided by the present invention are outlined below:

An electroporating drug delivering device using hollow needle electrode, comprises a drug delivering head, a control console, as well as a tube for connecting the drug delivering head and the control console;

the drug delivering head comprises a universal joint, a camera, an illuminating lamp, a drug delivery structure, an electric connector, a grille, a hollow needle electrode array, and a stretchable structure;

the hollow needle electrode array comprises at least two hollow needle electrodes with a distance to each other, and an electric pulse of a first polarity and an electric pulse of a second polarity are respectively applied on the hollow needle electrodes according to a time period, wherein, the hollow needle electrode corresponding to the electric pulse of the first polarity is surrounded by the hollow needle electrode corresponding to the electric pulse of the second polarity;

the at least two hollow needle electrodes are used for electroporation, mounted between the universal joint and the grille, connected with a power supply via the electric connector and connected with the molecular drug delivery structure such that a molecular drug is delivered into a tissue via the hollow needle electrodes;

the stretchable structure is tightly connected with ends of the hollow needle electrodes to cause the hollow needle electrodes connected thereto to shift to a stretched state from a retracted state, and the grille is in a closed state when in the retracted state, while the grille is in an open state when in the stretched state;

the control console comprises a display for observing images captured by the camera; a rocker for controlling the universal joint; a first remote switch for controlling the generation of electric pulses; a second remote switch for controlling the delivery of the molecular drug; a first switch for controlling the open and close of the grille; a second switch for controlling the stretchable structure to stretch out and retract; a structure for storing molecular drug, and a pump for delivering the molecular drug; a device for controlling the startup of the pump for delivering the molecular drug; and an electric pulse generator;

the control console is connected with the electric connector inside of the drug delivering head by means of a wire arranged inside of the tube, and the switches are integrated on a touch screen.

Preferably, the material of the hollow needle electrodes is one or more selected from stainless steel, platinum, gold, silver, copper or other conductive material.

Preferably, the hollow needle electrodes comprise an insulated part and/or a non-insulated part.

Preferably, the hollow needle electrodes comprise a straight or bent electrode, and the bent electrode comprises a bent part or a part with a radius of curvature.

Preferably, the diameters of the hollow needle electrodes are 0.01-1.5 mm.

Preferably, the hollow needle electrode array is arranged in a regular polygon shape or in a circle shape and comprises 4, 6, 8, 9, 16, 18, 24, 32 or 64 needles, and the distance between each two adjacent electrodes in the electrode array are equal.

Preferably, the hollow needle electrodes can be detached from the stretchable structure.

Preferably, the molecular drug to be released comprises one or more of chemotherapeutic drugs, polynucleotides, polypeptides and gene drugs.

Preferably, the chemotherapeutic drugs to be released includes one or more of bleomycin, neocarzinostatin, carboplatin, suramin, doxorubicin, serine adriamycin, cisplatin.

Preferably, the tissue is one of pancreas, larynx, nasopharynx, oropharynx, lung, heart, stomach, liver, kidney, muscle, breast, colon, prostate, thymus, testis and ovary.

Preferably, the hollow needle electrodes generates an electric field to be applied on the tissue, and the intensity of the electric field is 0.2V/cm to 20 kV/cm, the number of pulses is between 1 and 100, and the duration of each pulse is between 10 ms and 2000 ms.

A method of transmitting an electric field to a tissue comprises, positioning the hollow needle electrode array of the electroporating drug delivering device of the present invention within the region of a target tissue, and applying an electric current to the hollow needle electrode array.

A method of introducing a molecular drug into tissues or cells by an electroporating drug-delivering device using a hollow needle electrode comprises, positioning the hollow needle electrode array of the electroporating drug delivering device of the present invention within the region of a target tissue, applying an electric current to the hollow needle electrode array, and releasing the molecular drug into the tissue.

Use of introducing a molecular drug into tissues utilizing the electroporating drug delivering device of the present invention.

The beneficial effects of the present invention over the prior art are:

the present invention provides an electroporating drug-delivering device capable of entering human body with no damage or minimal damage, capable of monitoring in real time and accurately positioning, accurately controlling the administration dosage and depth, and capable of accurately adjust the electric field intensity. This device is a drug-administration device for electroporation in vivo with a wide universality, a good electroporating effect and no chemical pollution, reducing damages to the normal cells, enhancing the drug utilization efficiency, reducing the treatment time and mitigating the sufferings of patients during treatment. In addition, the electroporation device of the present invention is easy to operate, has high practicability and good therapeutic effects.

BRIEF DESCRIPTION OF THE DRAWINGS

For more clearly explaining the technical schemes in the embodiments of the present invention, the accompanying drawings used to describe the embodiments are simply introduced in the following. Apparently, the below described drawings merely show a part of the embodiments of the present invention, and those skilled in the art can obtain other drawings according to the accompanying drawings without creative work, wherein.

wherein, 1—drug-delivering head; 2—control wire and tube; 3—rocker for controlling the universal joint; 4—touch screen; 5—drug solution; 6—infusion pump; 7—camera display; 8—universal joint; 9—grille in closed state; 10—camera; 11—illuminating lamp; 12—hollow needle electrode array; 13—molecular drug delivery structure; 14—electric connector; 15—stretchable structure.

DETAILED DESCRIPTION OF EXEMPLARY EMBODIMENTS

In the following, the technical schemes in the embodiments of the present invention are explained clearly and fully, and apparently, the described embodiments are merely a part of the embodiments of the present invention, not all of the embodiments. Based on the embodiments of the present invention, all other embodiments obtained by one of ordinary skill in the art without creative work belong to the protective scope of the present invention.

Embodiment

In the following, the present invention is further explained in detail combining with the accompanying drawings and embodiments.

Control Console of the Drug-Delivering Device

Figure 1:
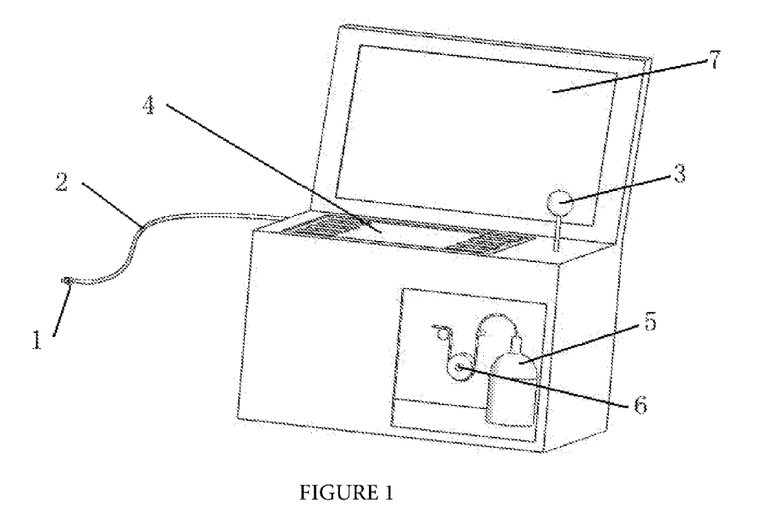
FIG. 1 is an overall schematic diagram of the control console and the drug-delivering head of the drug-administration device.

FIG. 1 is an overall schematic diagram of the control console and the drug-delivering head 1 of the drug-administration device. The control console comprises a display 7 for observing images captured by the camera, and a control unit 3 for controlling the universal joint. The control unit 3 for example may be a rocker, a steering ball or a similar device, for controlling the direction of the universal joint of the drug-delivering head. The control console comprises a first remote switch a for controlling the generation of electric pulses; a second remote switch b for controlling the delivery of the molecular drug; a first switch c for controlling the open and close of the grille; a second switch d for controlling the stretching out and retracting of the stretchable structure. Micro motors are located within the stretchable structure for controlling the open and close of the grille, the corresponding switches turn on or off corresponding motors by controlling the switches of the power supply and control the rotation directions of the motor shafts by controlling the polarity transformation of the electric currents so that controlling open and close of the grille and stretching out and retracting of the stretchable structure is achieved. The control console comprises a structure 5 for storing molecular drug, and a pump 6 for delivering the molecular drug; a device e for controlling the startup of the pump for delivering the molecular drug; the control console is connected with the electric connector inside the drug delivering head 1 by means of a wire 2 arranged inside the tube, and the buttons of the switch thereof are integrated on a touch screen 4. The duration of the electric pulse, the magnitude of voltage, addressing of the needle electrode or the switching mode may be controlled by the programs in the touch screen 4. The touch screen 4 shows a given value of the electric pulse voltage. The display 7 shows a real-time image of a camera, to assist the doctor to adjust the searching area and to determine the moment to apply the molecular drug. An alternating current powers the entire device; a pulse current generator module inside the device converts alternating current into pulsating direct current; a transformer inside the device converts alternating current into 5V direct current. The pulsating direct current and the 5V direct current are each connected to the electric connector in the drug-delivering head via the wire 2. The wire 2 comprises a control wire and a signal wire, for instance, the above switches b, c and d and the rocker 3 control the corresponding structures of the drug-delivering head via respective control wires, and the camera of the drug-delivering head transmits image data via the signal wire and the control console. The molecular drug in the molecular drug storing structure 5 is delivered to the drug delivering structure of the drug-delivering head via the tube 2.

Drug-Delivering Head of the Drug-Delivering Device

Figure 2:
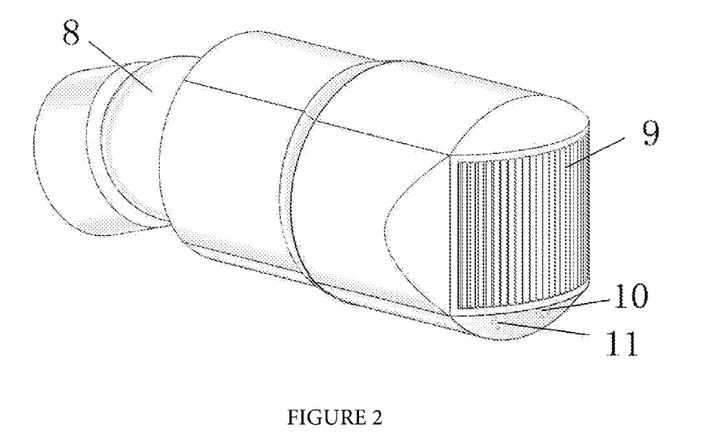
FIG. 2 is a schematic diagram of the drug-delivering head when the grille is in the closed state.

FIG. 2 is a schematic diagram of the drug-delivering head when the grille is in the closed state. The drug delivering head comprises a universal joint 8, a camera 10, an illuminating lamp 11, a molecular drug delivery structure 13, an electric connector 14, a grille 9, a hollow needle electrode array 12, and a stretchable structure 15; the molecular drug delivery structure 13, the electric connector 14, the hollow needle electrode array 12 and the stretchable structure 15 are packaged by a housing in the front of the drug-delivering head and connected with the wire and the tube 2 via the universal joint 8. The camera 10, the illuminating lamp 11 and the grille 9 are located in the front of the drug-delivering head outside of the housing. The universal joint is to adjust the deflecting direction of the front-end structure of the drug-delivering head, and an operator can control the deflecting of the universal joint by controlling the rocker on the control console. The camera is able to monitor images in front of the drug delivering head in real time, and in a preferred embodiment, the camera possesses a wide-angle lens. The illuminating lamp provides light source for the camera.

Figure 3:
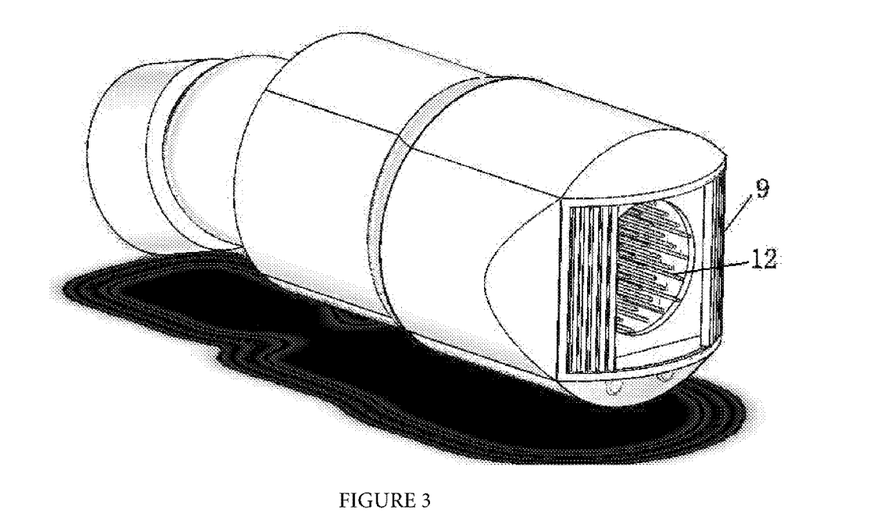
FIG. 3 is a schematic diagram of the drug-delivering head when the grille is half open and the electrode array is in the retracted state.

FIG. 3 is a schematic diagram of the drug-delivering head when the grille is half open and the electrode array is in the retracted state. The stretchable structure is tightly connected with ends of the hollow needle electrodes to cause the hollow needle electrodes connected thereto to shift to a stretched state from the retracted state, and the grille is in a closed state when in the retracted state, while the grille is in an open state when in the stretched state. The stretchable structure is connected with the power wire of the 5 V direct current of the wire 2 by means of the electric connector.

Hollow Needle Electrode Array

Figure 4:
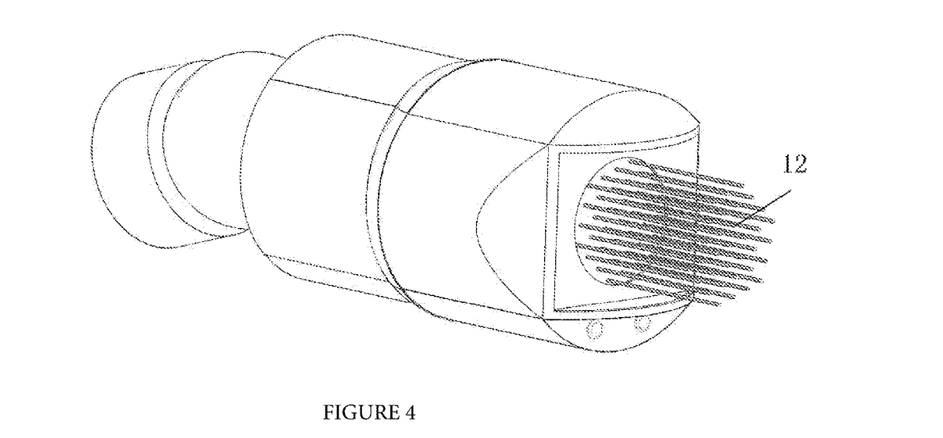
FIG. 4 is a schematic diagram of the drug-delivering head when the electrode array is in the stretched state.
Figure 5:
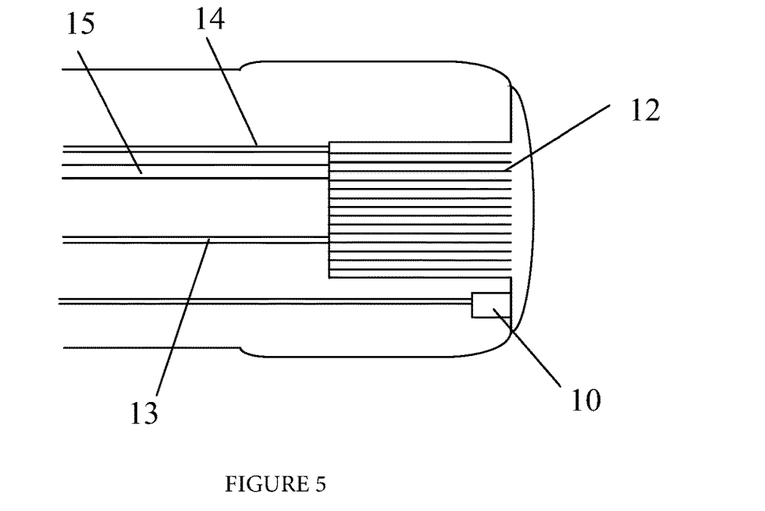
FIG. 5 is a cross-sectional schematic diagram of the drug-delivering head when the electrode array is in the retracted state.
Figure 6:
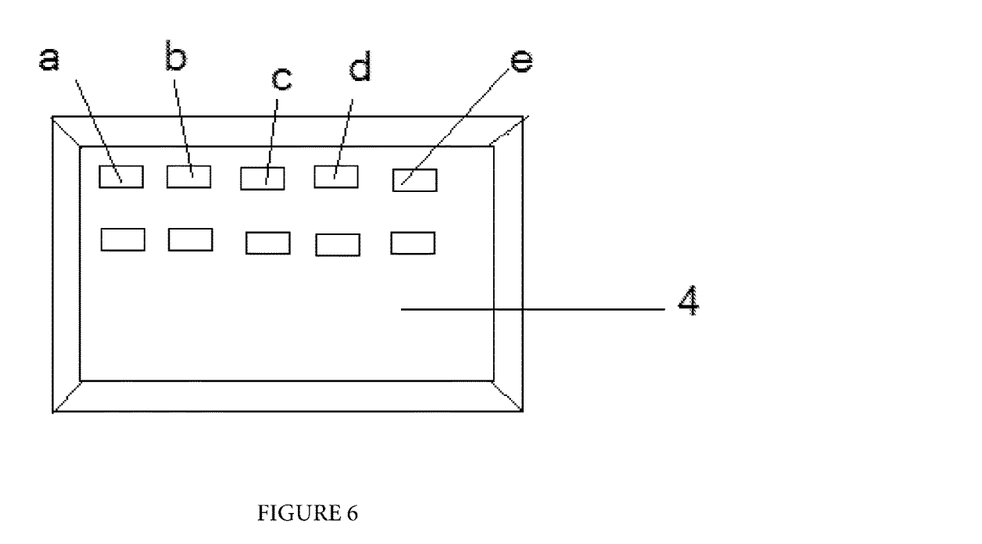
FIG. 6 is a schematic diagram of the bottoms of the starting units on the touch screen of the control console.

FIG. 4 is a schematic diagram of the drug-delivering head when the hollow needle electrode array is in the stretched state according to an embodiment of the present invention. The hollow needle electrode may be sharp, also may be blunt, and may have any required length. The material of the hollow needle electrode must be conductive, but not limited to be metal or of single material (that is, it may be employ a composite structure or a layered structure, for example, it may be employ a plastic needle or a ceramic needle plated with metal). The hollow needle electrode array comprises at least two hollow needle electrodes with a distance to each other, and an electric pulse of a first polarity and an electric pulse of a second polarity are respectively applied on the hollow needle electrodes according to a time period, wherein, the hollow needle electrode corresponding to the electric pulse of the first polarity is surrounded by the hollow needle electrode corresponding to the electric pulse of the second polarity. The ends of the hollow needle electrodes are tightly connected with the stretchable structure to cause the hollow needle electrodes connected to the stretchable structure to shift to the stretched state from the retracted state. The at least two hollow needle electrodes are mounted between the universal joint and the grille, connected with the pulsating current power supply via the electric connector and connected with the molecular drug delivery structure such that the molecular drug is delivered into a tissue via one or more hollow needle electrodes in the hollow needle electrode array. In different embodiments, the hollow needle electrodes may form an array with a square shape, a hexagon shape or a circle shape. However, it also may employ other shape.

In one embodiment, the present invention provides a method for applying an electroporating treatment to a tissue of a subject so as to introduce a molecular drug into cells of the tissue, and the method comprises steps as follow: providing a hollow electrode array, placing the electrode array surrounding the tissue to form a uniform and stable electric field, applying a high magnitude of electric signal pulse to the electrode to conduct electroporation on the tissue, the amplitude of the signal being in positive proportional to the distance between the electrodes.

It should be understood that, the electroporation on cells may be carried out in vivo, in vitro or ex-vivo. The electroporation also may be carried out utilizing monoplast, such as monoplast suspension or monoplast culture in vitro or ex-vivo.

Preferably, the molecular drug is introduced while electroporating, i.e. the time for delivering the molecular drug and the time for electroporating are synchronized, or the molecular drug or a treating agent may be dosed at any time.

For example, when directly injecting the drug into the tumor, it would be better to inject the drug in a "fan-shaped" manner. The "fan-shaped" means that, when injecting the drug, delivering the drug by means of changing the direction of the needle or by means of injecting the drug in multiple directions like an open hand, rather than injecting the drug in a bulk manner, to achieve the purpose of distributing the drug in the whole tumor more widely. Compared to the normal dosage amount in the art, when delivering (for example, injecting) the drug into the tumor, it would be better to increase the quantity of the drug-containing solution to ensure a proper distribution of the drug in the whole tumor. In practical application, the injection would better to be implemented very slowly surrounding the bottom in a fan-shaped manner. Although the gap pressure in the center of the tumor is very high, this part is often tumor necrosis area.

Electroporating Drug-Administration Method

Many kinds of different macromolecule compounds, including nucleic acids (plasmid DNA, linear DNA, small interfering RNA, antisense nucleic acids), proteins (peptide fragments, antibodies) and polynucleotides (including DNA, cDNA and RNA sequences), may enter into cells by means of electroporation utilizing the electroporation device of the present invention. The preferred plasmid is eukaryotic expression vector (pEGFP-C3), and those skilled in the art may choose various kinds of eukaryotic or prokaryotic expression vectors.

The drug in the present invention may be chemotherapy preparations or gene drugs with anti-tumor effect or cytotoxic effect. These drugs or preparations include bleomycin, neocarzinostation, suramin, doxorubicin, carboplatin, paclitaxel, mitomycin C and cisplatin. Other chemotherapy preparations are well known to those skilled in the art (for example, see *The Merck Index*). The gene drugs includes various of nucleic acids and protein drugs developed aiming at specific tumors.

Preferably, the tissue, on which the electroporation may be implemented by the electroporation device of the present invention, is one of pancreas, larynx, nasopharynx, oropharynx, lung, heart, stomach, liver, kidney, muscle, breast, colon, prostate, thymus, testis and ovary.

Any cell may be treated using the method of the present invention. The embodiments put forward herein explain the use of the method of the present invention in treating tumor cells such as cancer cells in pancreas or lung. Other cell proliferation dysfunctions also may be treated by means of the electroporation method of the present invention. The term "cell proliferation dysfunctions" means that, malignant and benign cell populations are different from the surrounding tissues in the morphology and genetic genes. The development of malignant cells (i.e. a tumor or cancer) is a result of several steps. The method of the present invention is useful to treat malignant tumors or various dysfunctions of organ systems, for example very useful when treating cells in pancreas or lung, also including cells in heart, stomach, liver, kidney, muscle, breast, colon, prostate, thymus, testis and ovary. Preferred subjects are human cells.

Specific Embodiment 1

The device of the present invention is used to deliver drugs to and treat tumor cells in vivo mice models. Firstly, the mouse breast cancer cells were cultured in culture medium, and then transplanted from the culture medium to the abdomens of the mice to develop subcutaneous tumors. When the tumors grew up to a diameter of 1 cm or larger, the electroporation treatments were carried out. Female mice of weight 230-250 g were tested, and 30 solid breast tumors in mice were treated. The breast tumors in mice without electroporation treatment were as control.

A treatment process comprised the following steps: (1) using alcohol solution to clean and disinfect the overall drug delivering head, checking whether the circuit is stable, whether the grille is able to open, whether the electrode array can stretch, whether each starting units are normal, and whether the control rocker of the universal joint is normal; (2) stretching the drug delivering head into the body, adjusting the entered area by means of the camera display, and identifying the site to be administered; (3) starting the control unit of the grill and opening the grill; (4) starting the control unit of the stretchable structure, stretching out the electrode array (the hollow needle electrodes are positioned along a circle with a diameter of 1 cm, and the diameter of the hollow needle electrode array is 1 cm) from the drug delivering head extends, and controlling the stretched length; (5) controlling the electrode array to direct against the tumor tissue by controlling the control rocker of the universal joint; and (6) injecting bleomycin (0.5 unit in 0.15 mL saline) around the mice tumors by starting the controller of the molecular drug delivery pump, starting electric pulses, switching the electrodes by the electric connector inside to the drug delivering head and applying six square wave electrical pulses, such that the pulse field can cover the tumors to the greatest extent. Electrical parameters were: central electric field intensity was pulses of 780 V/cm×6×99 ms with intervals of 1 s.

The results showed that, the treatment sites on almost all mice showed severe necrosis and edema. Tumor volumes in the treated group of mice were significantly reduced, while the tumor volumes in the control group of mice were significantly increased. Histological analysis on the tumor samples showed that, the treatment group had only vacuolation of necrotic tumor cells. Studies have shown that, the treatment with both electroporation and bleomycin acquired encouraging results.

The embodiments described above are only preferable embodiments, should not be concluded to limit this invention, and the implementations of the present invention should not be limited to these embodiments. It should be noted that, for those ordinary skilled in the art, any improvements or modifications without depart from the technical principle and conception of the present invention can be made, and should be covered by the protective scope of the present invention.

What is claimed is:

1. An electroporating drug delivering device comprising a drug delivering head, a control console, as well as a wire and a tube for connecting the drug delivering head and the control console; wherein
   the drug delivering head comprises a universal joint, a camera, an illuminating lamp, a molecular drug delivery structure, an electric connector, a grille, a hollow needle electrode array, and a stretchable structure; the molecular drug delivery structure, the electric connector, the hollow needle electrode array and the stretchable structure are packaged by a housing, and the universal joint connects with a rear end of the housing; the grille is located outside of a front end of the housing; the camera is to capture images in front of the drug delivering head, and the illuminating lamp provides light source for the camera;
   the hollow needle electrode array comprising at least two hollow needle electrodes with a distance to each other, and an electric pulse of a first polarity and an electric pulse of a second polarity are respectively applied on the hollow needle electrodes according to a time period, wherein, the hollow needle electrode corresponding to the electric pulse of the first polarity is surrounded by the hollow needle electrode corresponding to the electric pulse of the second polarity; the at least two hollow needle electrodes are used for electroporation, mounted between the universal joint and the grille, connected with a power supply via the electric connector and connected with the molecular drug delivery structure such that a molecular drug is capable of being delivered into a tissue via the hollow needle electrodes;
   the stretchable structure is tightly connected with ends of the hollow needle electrodes to cause the hollow needle electrodes connected thereto to shift to a stretched state from a retracted state, and the grille is in a closed state when the hollow needle electrodes are in the retracted state, while the grille is in an open state when the hollow needle electrodes are in the stretched state;
   the control console comprises a display for observing images captured by the camera; a control unit for controlling the universal joint to rotate; a first remote switch connected with the power supply for controlling the generation of electric pulses; a second remote switch for controlling the delivery of the molecular drug; a first switch for controlling the open and close of the grille; a second switch for controlling the stretchable structure to stretch out and retract; a structure for storing the molecular drug, and a pump for delivering the molecular drug; the control console is connected with the electric connector inside of the drug delivering head via the wire, and the molecular drug is delivered from the structure for storing the molecular drug to the molecular drug delivery structure via the tube.

2. The electroporating drug delivering device according to claim 1, wherein,
   the control unit is a rocker;
   and/or;
   the wire is arranged inside the tube.

3. The electroporating drug delivering device according to claim 1, wherein,
   a material of the hollow needle electrodes is one or more selected from stainless steel, platinum, gold, silver, copper or other conductive material;
   and/or;
   the hollow needle electrodes comprise an insulated part and/or a non-insulated part.

4. The electroporating drug delivering device according to claim 1, wherein, the hollow needle electrodes comprise a straight or bent needle electrode, and the bent needle electrode comprises a bent part or a part with a radius of curvature.

5. The electroporating drug delivering device according to claim 1, wherein, a diameter of each of the hollow needle electrodes are 0.01-1.5 mm.

6. The electroporating drug delivering device according to claim 1, wherein, the at least two hollow electrodes are a number of electrodes sufficient to form a circle shape or a regular polygon shape and wherein the hollow needle electrode array is arranged in the regular polygon shape or the circle shape, and the distance between each two nearest adjacent needle electrodes in the hollow needle electrode array are equal.

7. The electroporating drug delivering device according to claim 1, wherein, the hollow needle electrodes and the stretchable structure are detachably connected.

8. The electroporating drug delivering device according to claim 1, wherein, the molecular drug to be delivered comprises one or more of chemotherapeutic drugs, polynucleotides and polypeptides.

9. The electroporating drug delivering device according to claim 8, wherein, the drug to be delivered comprises chemotherapeutic drugs and/or cancer immunotherapeutic drugs, the chemotherapeutic drugs including one or more of bleomycin, neocarzinostatin, carboplatin, suramin, doxorubicin, serine adriamycin, cisplatin, and the cancer immunotherapeutic drugs including gene therapeutic drugs.

10. The electroporating drug delivering device according to claim 1, wherein, the tissue is one of pancreas, larynx, nasopharynx, oropharynx, lung, heart, stomach, liver, kidney, muscle, breast, colon, prostate, thymus, testis and ovary.

11. The electroporating drug delivering device according to claim 1, wherein, the hollow needle electrodes generate an electric field configured to be applied on the tissue, and the intensity of the electric field is 0.2V/cm to 20 kV/cm, the number of pulses is between 1 and 100, and the duration of each pulse is between 10 ms and 2000 ms.

12. A method of transmitting an electric field to a tissue comprises, positioning the hollow needle electrode array of the electroporating drug delivering device according to claim 1 within the region of a target tissue, and applying an electric current to the hollow needle electrode array.

13. A method of introducing a molecular drug into a tissue by an electroporating drug-delivering device comprises, positioning the hollow needle electrode array of the electroporating drug delivering device according to claim 1 within the region of a target tissue, releasing the molecular drug into the tissue, and applying an electric current to the hollow needle electrode array.

* * * * *